United States Patent [19]

Alagy et al.

[11] Patent Number: 4,926,001
[45] Date of Patent: May 15, 1990

[54] METHOD FOR THE THERMAL CONVERSION OF METHANE TO HYDROCARBONS OF HIGHER MOLECULAR WEIGHTS

[75] Inventors: Jacques Alagy, Charbonnieres; Christian Busson, Dardilly, both of France

[73] Assignee: Institut Francais du Petrole, Rueil-Malmaison, France

[21] Appl. No.: 927,980

[22] Filed: Nov. 7, 1986

[30] Foreign Application Priority Data

| Nov. 8, 1985 | [FR] | France | 85 16714 |
| Mar. 18, 1986 | [FR] | France | 86 03970 |
| Jun. 23, 1986 | [FR] | France | 86 09168 |

[51] Int. Cl.$^5$ .................................................. C07C 2/00
[52] U.S. Cl. .................................... 585/500; 585/943
[58] Field of Search ................................. 585/943, 500

[56] References Cited

U.S. PATENT DOCUMENTS

| 1,890,434 | 12/1932 | Krauch et al. | 585/943 |
| 1,917,627 | 7/1933 | Wulff | 585/943 |
| 2,022,279 | 11/1935 | Fuler | 585/943 |
| 2,645,673 | 7/1953 | Hasche | 585/943 |
| 2,679,544 | 5/1954 | Bills | 585/943 |
| 2,958,716 | 11/1960 | Lahr et al. | 585/943 |
| 2,985,698 | 5/1961 | Dechtold et al. | 585/943 |
| 3,192,280 | 6/1965 | Landgren | 585/943 |
| 3,244,765 | 4/1966 | Fauser | 585/943 |
| 3,333,873 | 6/1967 | Horn et al. | 585/943 |
| 3,819,724 | 6/1974 | Velcso | 585/943 |
| 4,144,444 | 3/1979 | Dementiev | 219/121 |

Primary Examiner—William R. Dixon, Jr.
Assistant Examiner—James M. Hunter, Jr.
Attorney, Agent, or Firm—Millen, White & Zelano

[57] ABSTRACT

The invention concerns an improved method for the thermal conversion of methane to hydrocarbons of higher molecular weights.

The method is based on the utilization of a multichannel system of ceramic material in which the charge and heating fluids or cooling fluids pass alternately through rows of channels, constituting a continuous assembly comprising a pyrolysis zone followed by a quenching zone.

17 Claims, 1 Drawing Sheet

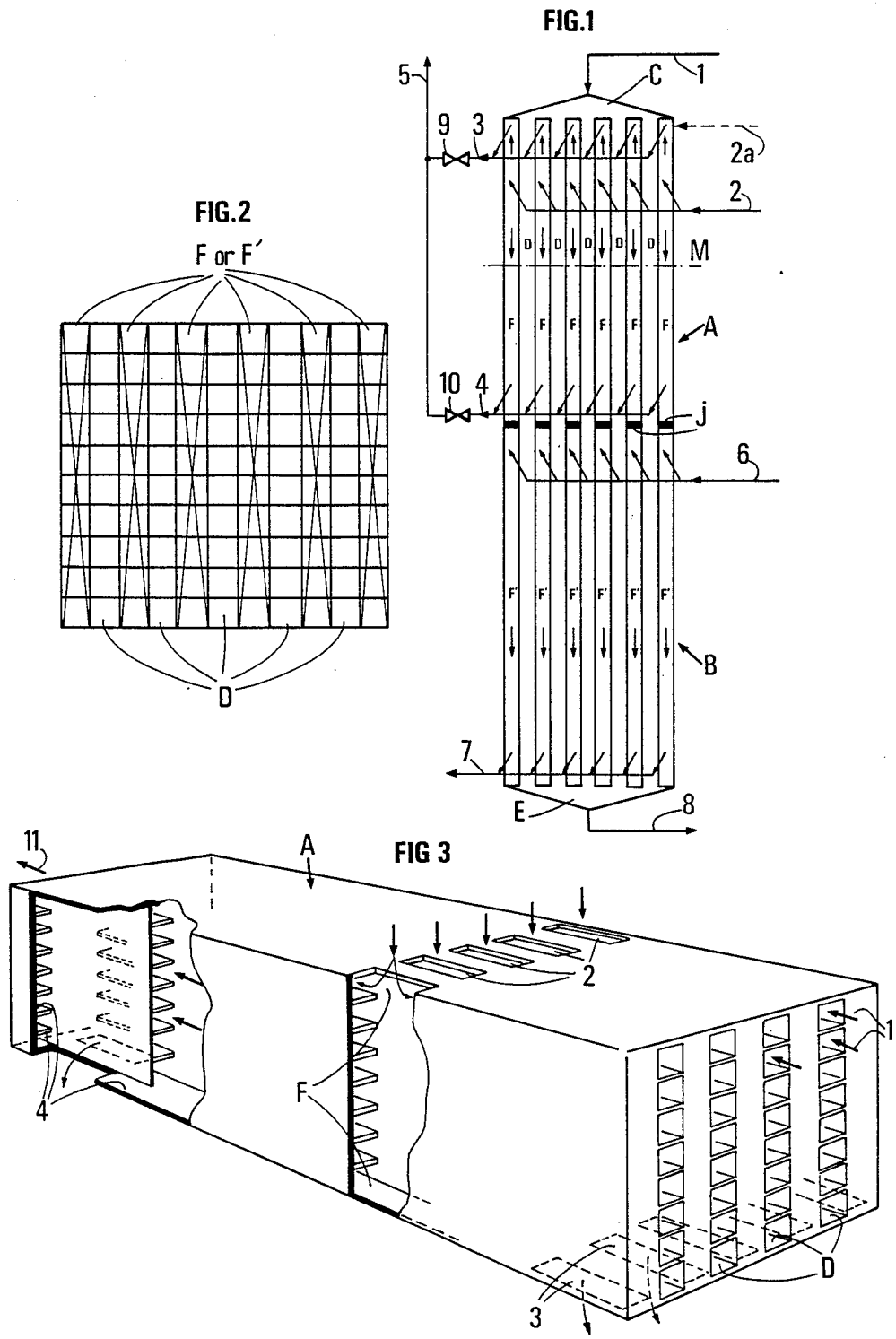

METHOD FOR THE THERMAL CONVERSION OF METHANE TO HYDROCARBONS OF HIGHER MOLECULAR WEIGHTS

BACKGROUND OF THE INVENTION

The invention concerns an improved method for the thermal conversion of methane to hydrocarbons of higher molecular weights.

Among the sources of methane are natural gases and refinery gases. The natural gases may or may not be associated with crude oil; their composition varies quite appreciably according to their source, but they generally contain a percentage by volume of methane between 60 and 95%. This methane is always associated with higher alkanes, which can be or even exceed 6 carbon atom hydrocarbons. Various cryogenic methods enable the gases once they have been freed from water and acid components to be separated into several fractions: nitrogen, liquefied natural gases from which the propane and butane fractions are separated, and a fraction consisting essentially of methane associated with a small quantity of ethane. This latter fraction is either reinjected into the wells to maintain the pressure which makes the crude petroleum rise, or conveyed as a combustible gas by gas pipeline, or else burned at the flare stack.

Other sources of methane are refinery gases which are of multiple origin: crude petroleum first distillation gas, hydroreforming gas, gas from various hydrotreatments, thermal cracking gas, catalytic cracking gas; all these gases contain in various proportions methane associated with a number of other gaseous components, such as light hydrocarbons, nitrogen, $CO_2$, etc.

Thus, for example, an effluent gas from a fluidized bed catalytic cracking unit comprises, after washing, about 30% by volume of methane. This gas is often fractionated by cooling under pressure to obtain two fractions, one comprising hydrogen, nitrogen, methane and a small part of ethylene, and the other fraction containing the major part of the initial ethylene with ethane, propane and propylene. This latter fraction can be advantageously conveyed to a Dimersol type unit, while the first fraction is returned to the refinery fuel gas network in which it is used as a fuel.

The conversion of methane to hydrocarbons of higher molecular weights is therefore of definite interest: thus, in remote natural gas or associated gas deposits, the conversion of methane to acetylene, ethylene and aromatics makes possible, by known methods, obtaining more easily transportable and/or valorisable liquid fractions.

For example, after separation of any solids formed, the aromatic compounds fraction can be separated, and the gaseous fraction then treated first in acetylene oligomerization and/or cyclisation units and then, after a further gas/liquid separation, the residual gas fraction of high ethylene content is treated in Dimersol type units which enable ethylene oligomers to be obtained.

On the refinery sites themselves, the conversion, even partial, of methane to more easily valorisable products also is of great economic interest.

Various methods of conversion of methane have already been suggested; thus U.S. Pat. No. 4,199,533 discloses a method for obtaining ethylene and/or ethane from methane, by reacting this product with chlorine at temperatures above 700° C. This method has the great disadvantage of using very corrosive gases, such as chlorine and hydrochloric acid, at high temperatures.

Among the thermal cracking processes that can convert methane, the so-called "Wulff process" consists in using refractory contact masses; first, the refractory mass is heated by the combustion in air of a fuel which can be the charge itself and then, secondly, the hydrocarbon to be cracked is decomposed by absorbing heat stored in the refractory material during the preceding period; this is therefore a batch process.

Electric arc and plasma processes are used essentially in the preparation of acetylene; their high electrical energy consumption makes their utilization difficult.

A third type of process, sometimes called autothermal, involves burning a part of the charge to supply the heat required for the cracking reaction; this type of process uses a burner in which about one-third of the hydrocarbon is burnt, the remainder being cracked. In view of the high thermal levels obtained, this type of process essentially produces acetylene and coke.

French patent No. 1,211,695 discloses a combined hydrocarbon pyrolysis method involving mixing methane with hot combustion gases containing no excess oxygen and then injecting into the mixture obtained paraffinic hydrocarbons with more than one carbon atom; according to this method a very small part of the methane can be converted to acetylene. There does not exist at present any industrial process using controlled heat transfer through a wall for converting methane to easily valorisable hydrocarbons, such as acetylene, ethylene and/or aromatic compounds.

SUMMARY OF THE INVENTION

An object of this invention is to fill this gap by providing a method for the thermal conversion of methane to hydrocarbons of higher molecular weights. More particularly, the invention involves using a multichannel continuous system made of ceramic material, preferably silicon carbide, of any shape but advantageously round, square or rectangular, comprising a plurality of parallel channels, forming rows, these channels being of any shape but advantageously polygonal and preferentially square or rectangular, and designed in a manner such that the charge to be treated passes through the rows of channels of order ... n-2, n, n+2, n+4, ... and the heat-exchange or cooling fluids pass through the other ranges of channels of order ... n-1, n+1, n+3, ... n being any number.

The choice of the fluid for the first and last row is immaterial, an essential feature being observance of a row alternance.

The rows of channels through which the charge is passed are uninterrupted over the total length of the assembly. The other rows of channels are divided into two successive parts by a partition at an intermediate point of their length so as to define two zones, a heat exchange fluid passing through the channels of the first zone (in the direction of flow of the charge to be treated) thereby determining the pyrolysis zone or reaction zone, a cooling fluid passing through the channels of the second zone (effluent outlet side) thereby determining a cooling zone or quenching zone.

The system thereby obtained therefore constitutes a continuous pyrolysis reactor and quenching exchanger assembly.

In a preferential embodiment of the invention, the heat exchange fluid enters the rows of channels designed to convey it, perpendicularly to the axis of these rows of channels, by means of an opening in one of the lateral walls of the channels concerned located on the periphery, and the channels of a same row are connected at the heat exchange fluid inlet by openings made in their lateral walls so that the heat exchange fluid passes through the totality of the channels intended for that purpose.

Preferentially, the heat exchange fluid arrives in the pyrolysis zone at an intermediate point of this zone, located at a distance from the beginning of this zone (the beginning being determined by the charge introduction point) representing 5 to 50% of the total length of this zone, and more preferentially 20 to 40% of this zone; in this way, the maximum supply of heat can be transmitted to the channels through which the charge passes at the location where the endothermal cracking and dehydrogenation reaction take place.

The total number of channel rows is not critical in this method; it obviously depends on the size of the pyrolysis reactor-quenching exchanger assembly and the dimensions of a unit channel. However, within the scope of the invention, the heat exchange or cooling fluids preferentially pass through the two rows of external channels.

The number of unit channels per row also is not determinant and depends on the overall size of the assembly and the size of a unit channel.

A unit channel has advantageously a section of between 9 and 900 mm$^2$ and preferentially between 25 and 100 mm$^2$; the length of a unit channel can vary according to the charges to be treated, the process temperature, the desired contact time and the temperature at which quenching takes place. The total length of a unit channel—comprising the pyrolysis zone and the quenching zone—is generally between 2 and 15 m and, preferably, between 5 and 10 m. In a particular embodiment of the method, each unit channel can be divided into a plurality of smaller elementary channels. Within the scope of the invention, the continuous pyrolysis reactor—quenching exchanger assembly can be made either in the form of a single unit, or else by contiguously placing side by side unit elements of identical shape, which are assembled to one another by any suitable means, such as for example, with flanges. The utilization of ceramics, and more particularly silicon carbide, an easily extrudable material, makes the utilization of such assemblies or assembly elements easy.

The charges to be treated have a dwell time in the reaction zone of between 5 and 1000 milliseconds, and more advantageously between 200 and 500 milliseconds; the temperature of the walls in the reaction zone can be raised to a maximum value of the order of 1,500° C.

Any refractory ceramics resisting temperatures higher than 1150° C. can be used within the scope of the invention; silicon carbide, which has good thermoconductivity and is easily processed by extrusion, is the ceramic used preferentially.

Numerous ceramic indirect heat exchangers are disclosed in the prior art; their field of application concerns essentially the turbine engines, in which the exchanger material must withstand temperatures of the order of 1200° to 1400° C. For example, French patent No. 2,436,956, U.S. Pat. No. 4,421,702, Japanese patent application Nos. 59-046,496 and 59-050,082, as well as French patent Nos. 2,414,988 and 2,436,958 (addition patent to the preceding one), may for example be cited, the last of these patents disclosing a method for manufacturing of a ceramic indirect heat exchange element that can be advantageously used within the scope of the invention, subject to adaptation.

The method of the invention enables methane to be converted thermally to acetylene, ethylene and benzenic products, essentialy, because of the following characteristics:

the ability to operate continuously at wall temperatures reaching 1500° C.

very high exchange surface (s) to reaction volume (v) ratio, which is greater than 200 m$^{-1}$ and can attain 1000 m$^{-1}$.

These two characteristics enable a very high thermal flux density to be obtained at a high temperature level.

Silicon carbide, the preferentially used ceramic material within the scope of the invention, is completely inert to the various cracking products formed, whereas this is not the case with refractory steels nor even steels covered with layers of refractory materials.

The hydrocarbon charges usable within the scope of the invention are gaseous charges under normal temperature and pressure conditions, comprising a molar percentage of methane of between 10 and 99%, for example, between 20 and 99% and preferentially between 30 and 80%.

The remainder of the charge can consist of saturated or unsaturated aliphatic hydrocarbons, comprising a number of carbon atoms equal to or greater than two, such as for example, ethylene, ethane, propane or propylene; other gaseous components of the charge can be nitrogen, carbon dioxide or carbon monoxide or, preferably, hydrogen whose presence reduces the formation of coke. The molar proportion of hydrogen can be 1 to 90%.

While remaining within the scope of the invention, dilution steam can be added to the charges defined hereinbefore; the weight ratio of the dilution steam to the hydrocarbon charge is on the order of 0.1 to 1.

The heat exchange fluids usable in the pyrolysis zone can be any fluids thermally stable at temperatures of the order of 1200° to 1500° C.; preference is given to using burner combustion gases or hot waste gases from other processes.

The fluids that may be used for cooling effluents in the quenching zone can be for example air, alone or mixed with combustion gases, or else low temperature steam at low pressure.

BRIEF DESCRIPTION OF THE DRAWINGS

The invention will be better understood by the description of some embodiments given by way of illustration but being in no way limitative, with the aid of the appended figures:

FIG. 1 represents an embodiment of the method according to the invention, along a longitudinal cross-section of the reactor-quenching exchanger assembly;

FIG. 2 represents a cross-section of an element of the assembly of rectangular cross-section comprising square unit channels;

FIG. 3 represents an exploded perspective view of a module representative of the pyrolysis zone part, of rectangular cross-section.

DETAILED DESCRIPTION OF THE DRAWINGS

FIG. 1 represents a multichannel assembly comprising a pyrolysis zone (A) and a quenching zone (B). The mixture constituted by the hydrocarbon charge to be treated and if necessary by steam, is preheated in a preheating zone not shown in the figure.

This preheating zone can be either of conventional type, such as a convection system, or a multichannel type heat exchanger, according to the technology described for the pyrolysis zone, the heat exchange fluid passing through this preheating zone can advantageously consist of a heat exchange fluid from the outlet of the pyrolysis zone. At the outlet of this preheating zone, the mixture enters through line (1) the pyrolysis zone (A) where it is distributed by means of a distributor (C) in the plurality of reaction channels (D).

The broken line (M) indicates about half the length of the pyrolysis zone (A); the heat exchange fluid input line (2) reaches zone (A) at an intermediate point located between (M) and (C) at a distance from the beginning of the pyrolysis zone (A) representing 5 to 50% of the total length of this zone and preferably 20 to 40% of the length of this zone; this heat exchange fluid is preferentially combustion gases coming for example from a burner not shown in the figure. These combustion gases enter the zone (A) and are distributed in the plurality of heating channels indicated by (F); they preferentially pass through these series of channels (F), counter-current with respect to the reaction mixture circulating in the channels (D) in the part of the zone (A) located between the combustion gases inlet (2) and their upper outlet (3), and circulate co-current with respect to the reaction mixture between inlet (2) and lower outlet (4) for the combustion gases. The combustion gases outlet lines (3) and (4) comprise flow rate regulating systems (9 and 10), such as for example butterfly valves, enabling the respective flow rates of the combustion gases between outlets (3) and (4) to be regulated.

In the particular case when it is desired that the heat exchange fluid arrives at the beginning of zone (A), the latter may then not comprise any inlet (2), or else it can be shut off, the fluid then enters through line (2a) and the fluid travels entirely co-current with respect to the reaction mixture, and it leaves only through line (4), the outlet (3) then being suppressed.

In the more general case described above, the combustion gases leaving through lines (3) and (4) are joined and passed through line (5) to the preheating zone (by convection, for example).

The closure of channels (F) by tight closing devices (J) delimits the pyrolysis (A) and quenching (B) zones. The cooling fluid preferentially enters the quenching zone (B) through line (6) located at the very beginning of the exchanger and circulates in the channels (F') parallel to channels (D) co-current with respect to the reaction effluents, and leaves the exchanger through line (7). If necessary, the direction in which the cooling fluid circulates can be reversed, in which case the fluid enters the exchange zone (B) through line (7) and, after having cooled the reaction effluents counter-current, leaves (B) through line (6).

The reaction effluents cooled thereby collect in zone (E) and are recovered through line (8). According to the nature of the charges treated, these effluents can if necessary be subjected to a second quenching by direct addition of cold fluid, according to a known process. The subsequent treatments of the effluents are part of the prior art and are outside the scope of this invention.

FIG. 2 represents a cross-section of a reactor element of rectangular cross-section comprising square unit channels. In this figure, the reaction channels through which the charge to be treated passes are represented by the rows of channels (D), as depicted in FIG. 1.

The channels through which the heat exchange fluid passes are represented by the hatched rows of channels (F), as depicted in FIG. 1.

FIG. 3 represents an exploded perspective view of a module of the pyrolysis zone part (A) of the pyrolysis zone - quenching zone assembly. For the sake of clarity in this figure, the charge distributor (C) depicted in FIG. 1 is not shown. The designations used for the various elements are those of FIG. 1.

In this figure, the pathway of the charge to be treated is represented by the arrows (1); the charge enters the pyrolysis zone (A), is distributed into the plurality of unit channels (D), and passes longitudinally through the pyrolysis zone (A) in these multichannels (D) and leaves zone (A) by the these same multichannels at (11); these multichannels (D) are prolonged into the quenching zone not shown in the figure, which is immediately next to zone (A).

The pathway followed by the heat exchange fluid is represented by the arrows opposite the openings (2); the heat exchange fluid enters (A) by the openings (2) located in the first half of zone (A); it is distributed into the plurality of the unit channels (F), one part of this fluid passes through these channels counter-current with respect to the charge circulating in channels (D) and leaves (A) by the openings (3); the other part of this fluid circulates in channels (F) co-current with respect to the charge and leaves (A) by openings (4).

The example which follows is used to illustrate the invention but does not limit its scope.

In accordance with this invention, a still more improved form of using the method can be provided.

According to this embodiment, the effluent of a plasma torch fed by a plasmagene gas is added to the preheated gas containing methane which constitutes the process reagent. For it is known that by passing a so-called plasmagene gas through an electric arc, a particular reaction medium is created which is electrically neural but rich in ions, electrons, atoms and/or excited molecules. The plasmagene gas can be for example hydrogen, argon, steam, nitrogen, methane or any other standard gas or mixture of several of these in variable proportions. It can be in particular all or part of the gas feeding the pyrolysis zone.

According to a preferred embodiment of the invention, a part of the gas constituting the charge may be taken, before or after reheating, preferably after reheating, and conveyed to the plasma torch. The torch effluent is then immediately injected into the body of the remaining reaction fluid just before it enters the pyrolysis zone.

To this end 1% to 20% of the charge may be used but a continuous source of plasmagene gas can also be used. The effect of this seeding by means of plasma promotes the initial pyrolysis stages and therefore greatly facilitates the conversion of methane to hydrocarbons of higher molecular weights.

Thus, it becomes possible to operate at a lower temperature than when it there is no seeding, that is, for example, at an average temperature in the pyrolysis reactor lower by about 100°.

Although the thermal level is lower, the methane conversion rate is maintained. On the other hand the tendency to form acetylenic compounds is reduced and the tendency to form olefinic and aromatic compounds is increased.

Subject to this reserve, the average pyrolysis temperature is usually between 600° and 1300° C. The object of quenching is to bring the temperature of the mixture down to below 400° C., for example, 200°-350° C. or lower.

Furthermore, a still more improved form of using the method has also been discovered.

According to this embodiment, whose utilization is easy, one adds to the preheated gas containing methane and constituting the process reagent, at least one initiator reactant chosen from the group formed by oxygen, ozone and hydrogen peroxide in suitable proportions with respect to the quantity of reagent introduced into the reaction zone. The initiator reagent is introduced into the mixture of preheated gas, preferably in a relatively small quantity compared with that of methane, before introducing the reaction mixture into the pyrolysis zone.

Without wishing to be tied to any theory, it can be theorized that the initiator reagent, introduced into the preheated charge generally at at least 300° C. and preferably at 500° to 600° C., promotes the formation of radicals, in particular methyl radicals and thus promotes the start up of the methane conversion reaction at a lower temperature, which enables a better yield of the desired ethylene and aromatic products obtained.

It is therefore not desirable to have too great a quantity of initiator reagent, as this might lead to the formation of a large quantity of radicals and the excessive formation of byproducts, in particular carbon oxides (CO, $CO_2$).

The quantity of initiator reagent introduced into the preheated gas mixture, expressed in atom-gram percentage of oxygen introduced, with respect to the quantity of methane expressed in mol, is generally 0.01% to 10% and preferably 0.1% to 1%.

According to a preferred embodiment of the invention, the initiator reagent is substantially pure oxygen (that is, containing less than 1% by volume of impurities), or oxygen diluted with an inert gas such as, for example, nitrogen or argon, or else a more complex gas mixture containing oxygen such as, for example, air, or air enriched with oxygen, or air diluted with an inert gas. It is also possible to introduce the initiator reagent by diluting it previously with a portion of the gaseous mixture to be treated.

When ozone is used, it can be used in a substantially pure form or diluted with a gas as mentioned above for oxygen. For example, a mixture of oxygen and ozone or ozonized air can be used.

When hydrogen peroxide is used, it can be used in a substantially pure form or in diluted form. It is also possible to use aqueous hydrogen peroxide, sometimes called "oxygenated water", with the proviso that the quantity of water then introduced into the reactor remains within the limits specified above.

It is possible to preheat the initiator reagent before its introduction, for example, up to a temperature of 150° C.

The effect of introducing at least one initiator reagent is to largely promote the conversion of methane to hydrocarbons of high molecular weight. The quantities introduced being relatively small, only a small proportion of carbon oxides is formed. This slight loss is very largely compensated for by the beneficial reaction initiation effect, which allows operation at lower temperatures and shorter dwell times of the charge to be treated in the reaction zone. Thus, in this particular case, it becomes generally possible to operate, for example, at an average temperature in the pyrolysis reactor lower by about 70° to about 100° than those involved when the initiator reagent is absent. The dwell time in the reaction zone can also be slightly reduced by the utilization of an initiator reagent.

Any refractory ceramic withstanding the maximum temperature of the heat exchange fluid can be used within the scope of this invention. By way of non-limitative examples can be cited the following ceramics: silicon carbide, mullite, cordierite and zircon-mullite.

EXAMPLE 1

In this example, a refinery fuel gas from a fluidized bed catalytic cracking unit was subjected to pyrolysis. The molar composition of this mixture, having previously been washed in order to remove its acid components, was as follows:

| Compound | Molar % |
| --- | --- |
| $H_2$ | 10 |
| $N_2$ | 12 |
| $CH_4$ | 32 |
| $C_2H_4$ | 15 |
| $C_2H_6$ | 14 |
| $C_3H_6$ | 11 |
| $C_3H_8$ | 6 |

This mixture is divided into two parts, after compression under 30 bars and cooling to $-100°$ C.; the head part (A) represents by volume 57% of the mixture and has the following molar composition:

| Compound | Molar % |
| --- | --- |
| $H_2$ | 17.5 |
| $N_2$ | 21.1 |
| $CH_4$ | 56.1 |
| $C_2H_4$ | 5.3 |

This fraction was preheated to 600° C. and cracked in an installation in accordance with the invention, comprising a silicon carbide multichannel pyrolysis zone, 3 m long, and whose unit channels have a square section of 100 mm². A heat exchange fluid consisting of burner combustion gases at 1400° C. was passed into the channel designed for the purpose at a rate such that the temperature of the effluent mixture at the outlet of the pyrolysis zone was 1200° C.; the dwell time of the charge in this zone was 300 ms. The quenching zone was fed with air as the cooling fluid. At the outlet of the quenching zone, the effluent gases were at 250° C.

By cooling to ambient temperature and separating the liquid and gaseous phases, the following products were obtained per 100 mol of charge:

| Products | Quantity |
| --- | --- |
| $H_2$ | 52.5 Mols |
| $N_2$ | 21.1 Mols |
| Carbon black | 8.96 g |
| Aromatics | 44.8 g |
| $CH_4$ | 28.1 Mols |
| $C_2H_2$ | 3.69 Mols |
| $C_2H_4$ | 13.92 Mols |

28 mols of methane, or 50% of the methane introduced were therefore converted during cracking, with a selectivity of 61% as regards formation of ethylene and 26% as regards formation of acetylene.

EXAMPLE 2

The following example illustrates non-limitatively the advantages of using a plasma torch to seed a charge rich in methane.

A charge identical with that of example 1 was treated:

| Compound | Molar % |
|---|---|
| $H_2$ | 17.5 |
| $N_2$ | 21.1 |
| $CH_4$ | 56.1 |
| $C_2H_4$ | 5.3 | in an identical equipment.

This mixture was preheated to 600° C. On leaving the preheating zone 5% of the flux leaving the preheating exchanger was taken and this divided fraction passed to a plasma torch. The plasma generated was reinjected into the gaseous flow downstream of the sampling point at the inlet of the channels through which the reagent to be pyrolized passes.

With a view to compensating for the endothermal nature of the pyrolysis reaction, combustion gases at 1300° C. (or 100° C. lower than the case of example 1) were passed into the channels designed for the heating fluid.

The pyrolyser outlet temperature established itself at about 1100° C. The dwell time of the charge in the pyrolysis zone was 250 ms, that is, a shorter duration compared to that of the reference example. Quenching took place with air as in the reference example so as to cool the gases down to 250° C.

After complete cooling and separation of the solid, liquid and gaseous phases, the following distribution of products was obtained per 100 mols of charge.

$H_2$: 51.5 mols
$N_2$: 21.5 mols
Carbon black: 6 g
Aromatics: 66 g
$CH_4$: 26.7 mols
$C_2H_2$: 2 mols
$C_2H_4$: 15.3 mols Table I gives opposite one another the operating conditions and results respectively for the reference example and for the example illustrating the improvement provided here.

TABLE 1

| Comparison of two tests: with and without plasma torch | | |
|---|---|---|
| | Reference case without plasma torch | Case with plasma torch |
| Average temperatures in pyrolysis zone | 950° C. | 850° C. |
| Dwell time | 300 ms | 250 ms |
| Methane conversion | 50% | 52.5% |
| Yields (mols) | | |
| $C_2H_2$ | 25% | 14% |
| $C_2H_4$ | 60% | 67% |
| Aromatics | 12% | 17% |
| Coke | 3% | 2% |

The beneficial effect of using the plasma torch is seen: maintenance of methane conversion despite a lower average pyrolysis temperature and a shorter dwell time, increase of selectivity in conversion of methane to ethylene or aromatics, drop of selectivity as regards coke and acetylene, products which are not required here.

EXAMPLE 3

The following example illustrates non-limitatively the advantages of using an initiator reagent introduced into a charge rich in methane.

A charge with the following composition was treated:

| Compound | Molar % |
|---|---|
| $CH_4$ | 95 |
| $C_2H_6$ | 5 |

The charge was treated in equipment identical with that used in example 1. The charge was preheated to 600° C.

Two tests were carried out, one with introduction of oxygen and the other in a manner identical to the preceding one with the exception that oxygen was not introduced.

In the first test, at the outlet of the preheating zone, a quantity of oxygen representing 0.5% in mol of oxygen with respect to the methane (or 1% in gram-atoms of oxygen with respect to the methane) was introduced into the mixture, at the inlet of the channels designed for the passage of reagent and upstream of the point at which the heat exchange fluid is introduced.

With a view to compensate for the endothermal nature of the pyrolysis reaction, combustion gases at 1350° C. were passed into the channels designed for the heating fluid.

In the comparative test, performed without addition of oxygen to the charge, the combustion gases used had a temperature of 1425° C.

The pyrolysis outlet temperature established itself at about 1150° C. in the first test with oxygen and about 1210° C. in the second test without oxygen.

The dwell time of the charge in the pyrolysis zone was 250 milliseconds (ms) in the first test with oxygen and 300 milliseconds in the second test without oxygen. Quenching was obtained with air as the cooling fluid so as to cool the gases down to 250° C.

After complete cooling and separation of the solid, liquid and gaseous phases, the distribution of the products obtained per 100 mols of charge in each of the two tests was determined and is given in Table 2 below.

TABLE 2

| Products | Test 1: with introduction of oxygen | Test 2: without introduction of oxygen |
|---|---|---|
| $H_2$ | 64.33 mols | 62.61 mols |
| CO | 1 mols | 0 |
| Carbon black | 4 g | 10 g |
| Aromatics | 66 g | 58.5 g |
| $CH_4$ | 44 mols | 47.5 mols |
| $C_2H_2$ | 4.46 mols | 7.03 mols |
| $C_2H_4$ | 22.84 mols | 19.06 mols |

Table 3 below gives the operating conditions and the results for the two tests.

TABLE 3

| Conditions | Test 1 with introduction of oxygen | Test 2 without introduction of oxygen |
|---|---|---|
| Average | 900° C. | 975° C. |

TABLE 3-continued

| Conditions | Test 1 with introduction of oxygen | Test 2 without introduction of oxygen |
|---|---|---|
| temperature in pyrolysis zone | | |
| Dwell time | 250 ms | 300 ms |
| Methane conversion | 53.7% | 50% |
| Yields (mols) | | |
| $C_2H_2$ | 17.5% | 29.6% |
| $C_2H_4$ | 70.0% | 59.2% |
| Aromatics | 9.95% | 9.47% |
| Coke | 0.65% | 1.75% |

The beneficial effect of the introduction of a small quantity of oxygen is seen: maintenance of methane conversion despite a lower average pyrolysis temperature and shorter dwell time, and an increase in selectivity of conversion of methane to ethylene or aromatics with a drop in selectivity as regards undesirable coke and acetylene.

What is claimed:

1. A method for the thermal conversion of methane to hydrocarbons of higher molecular weight in a continuous multichannel zone of ceramic material, consisting of a plurality of adjacent channels, said channels forming alternate rows of two different sets, the channels of the rows of the first set having means for introducing a fluid and means for discharging same, said channels extending over the entire length of the zone and the channels of the rows of the second set also extending over the entire length of the zone and being divided in at least one first and at least one second section, not communicating with one another, by an intermediate partition, each section having fluid introduction and discharge means, the channels of the rows of the first set not communicating with the channels of the rows of the second set, said method comprising circulating a gaseous mixture containing a molar percentage of methane of between 10 and 99% in the channels of the rows of the first set, circulating a heat exchange fluid in the channels of the first section of the rows of the second set, circulating a cooling fluid in the channels of said second section of the rows of the second set such that conversion of methane to higher hydrocarbons comprising a major amount of ethylene and aromatics takes place, and collecting said hydrocarbons of higher molecular weight at the end of the channels of the rows of the first set, wherein activated species of methane from a plasma torch are added to the gaseous mixture before said gaseous mixture is introduced into the channels of the rows of the first set.

2. A method according to claim 1 in which the heat exchange fluid is introduced into the channels of said first section of said second set perpendicularly to the axis of these channels, at an intermediate point located at a distance from the beginning of this section (charge feed side) representing 5 to 50% of the total length of the channels of this section, and the heat exchange flow is withdrawn partly upstream and partly downstream of said intermediate point.

3. A method according to claim 1 in which the cooling fluid is circulated in the channels of the second section co-current with respect to the gaseous mixture circulating in the channels of the rows of the first set.

4. A method according to claim 1 in which the gaseous mixture containing a molar percentage of between 10 and 99% of methane is diluted with steam, the steam to mixture ratio being about 0.1 to 1.

5. A method according to claim 1, in which the plasma torch is fed by hydrogen, argon, steam, nitrogen or methane gas.

6. A method according to claim 1, in which the gaseous mixture contains 20 to 99% of methane.

7. A method according to claim 1, in which the mixture further contains hydrogen.

8. A method according to claim 1, wherein the ceramic material is silicon carbide, mullite, cordierite or zirconmullite.

9. A method according to claim 1, wherein the ceramic material is silicon carbide.

10. A method according to claim 1, wherein at least one initiator reagent comprising oxygen, ozone or hydrogen peroxide is introduced into the gaseous mixture prior to circulation of the mixture into the channels of the rows of the first set.

11. A method for the thermal conversion of methane to hydrocarbons of higher molecular weight in a continuous multichannel zone of ceramic material, consisting of a plurality of adjacent channels, said channels forming alternate rows of two different sets, the channels of the rows of the first set having means for introducing a fluid and means for discharging same, said channels extending over the entire length of the zone and the channels of the rows of the second set also extending over the entire length of the zone and being divided in at least one first and at least one second section, not communicating with one another, by an intermediate partition, each section having fluid introduction and discharge means, the channels of the rows of the first set not communicating with the channels of the rows of the second set, said method comprising circulating a gaseous mixture containing a molar percentage of methane of between 10 and 99% in the channels of the rows of the first set, circulating a heat exchange fluid in the channels of said first section of the rows of the second set, circulating a cooling fluid in the channels of said second section of the rows of the second set such that conversion of methane to higher hydrocarbons comprising a major amount of ethylene and aromatics takes place, and collecting said hydrocarbons of higher molecular weights at the end of the channels of the rows of the first set, wherein an effective amount of at least one initiator reagent comprising oxygen ozone or hydrogen peroxide is introduced into the gaseous mixture, said mixture being previously heated to a temperature of at least 300° C., before introducing said mixture into the channels of the rows of the first set, said initiator reagent being introduced in a quantity expressed in gram-atom oxygen percentage with respect to the quantity of methane expressed in mol of 0.01 to 10%.

12. A method according to claim 11 in which the quantity of initiator reagent is 0.1 to 1%.

13. A method according to claim 11, wherein the initiator is oxygen.

14. A method according to claim 11, wherein the gaseous methane is preheated to 300° C. prior to addition of the initiator reagent.

15. A method according to claim 14, wherein the initiator is oxygen.

16. A method according to claim 15, wherein the oxygen is substantially pure $O_2$, or oxygen diluted with an inert gas.

17. A method according to claim 15, wherein the oxygen is diluted with air, with air enriched with oxygen or with air diluted with an inert gas.

* * * * *